United States Patent [19]

Martin et al.

[11] 4,031,224

[45] June 21, 1977

[54] 1,3-DIHYDRO-HETEROARYLSPIRO (ISOBENZOFURAN)S

[75] Inventors: Lawrence Leo Martin, Lebanon; Brian J. Duffy, Flanders, both of N.J.

[73] Assignee: American Hoechst Corporation, Bridgewater, N.J.

[22] Filed: Apr. 29, 1976

[21] Appl. No.: 681,509

[52] U.S. Cl. .................... 424/267; 260/250 B; 260/293.57; 260/293.58; 260/294.8 B; 260/295 T; 260/296 T; 260/306.8 F; 260/307 R; 260/309; 260/326.34; 260/326.5 CA; 260/326.5 SM; 260/322.2 A; 260/332.3 P; 260/347.4; 260/347.7; 424/250; 424/270; 424/272; 424/273; 424/274; 424/275; 424/285

[51] Int. Cl.² ...................... C07D 405/14

[58] Field of Search ..... 260/250 B, 293.57, 293.58, 260/294.8 B, 295 T, 296 T, 306.8 F, 307 R, 309, 326. 34, 326.5 CA, 326.5 SM, 332.2 A, 332.3 P, 347.4, 347.7; 424/250, 267, 270, 272, 273, 274, 275, 285

[56] References Cited

UNITED STATES PATENTS 3,959,475  5/1976  Bauer et al. ...................... 424/267
3,980,787  9/1976  Klioze et al. ..................... 424/267

*Primary Examiner*—Cecilia M. S. Jaisle
*Attorney, Agent, or Firm*—Curtis, Morris & Safford

[57] ABSTRACT

Novel 1,3-dihydro-heteroarylspiro[isobenzofuran]s and methods of preparing same are described. These compounds are useful as antidepressants and tranquilizers.

35 Claims, No Drawings

1,3-DIHYDRO-HETEROARYLSPIRO (ISOBENZOFURAN)S

This invention relates to 1,3-dihydro-heteroarylspiro[isobenzofuran]s and their pharmaceutically acceptable salts which are useful as antidepressants and tranquilizers, to methods of preparing the same, to methods of treatment with pharmaceutically effective amounts thereof, and to pharmaceutical compositions containing such compounds as essential active ingredients.

To the best of our knowledge, we were the first to synthesize the compounds of this invention. Subsequent to commencing our work relating to this invention, Marxer et al., J. Org. Chem. Vol. 40, No. 10, 1427 (1975), described a synthesis of spiro[isobenzofuran-1(3H),4'-piperidines] and spiro[isobenzofuran-1(3H),3'-piperidines], including 1'-methyl-1,3-dihydro-3-(2-thienyl)-3-hydroxyspiro[isobenzofuran-1,4'-piperidine]. The compounds described therein, for which no utility was suggested, are outside the scope of this invention.

Other 1,3-dihydrospiro[isobenzofuran]s are described by Bauer and Kosley, Jr. in U.S. Patent Application Ser. No. 424,080, filed Dec. 12, 1973, now U.S. Pat. No. 3,962,259 and Ser. No. 502,650, filed Sept. 9, 1974, now U.S. Pat. No. 3,595,475 which is a continuation-in-part of Ser. No. 424,117, filed Dec. 12, 1973, now abandoned, and Bauer and Ong in U.S. patent application Ser. No. 501,669, filed Aug. 29, 1974. However, the compounds described in the aforesaid applications do not suggest the compounds of this invention.

The compounds of the invention have the formula

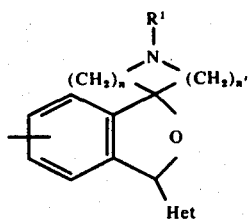

wherein R is hydrogen, alkyl of from 1 to 6 carbon atoms, alkoxy of from 1 to 6 carbon atoms, trifluoromethyl or halogen; $R^1$ is hydrogen, alkyl of from 1 to 6 carbon atoms, phenalkyl of from 7 to 9 carbon atoms, benzoylalkyl of the formula $-(CH_2)_m-COPhR$, phenoxycarbonyl, alkoxycarbonyl of from 2 to 7 carbon atoms, alkenyl of from 2 to 6 carbon atoms, cycloalkylcarbonyl of from 4 to 7 carbon atoms or cycloalkylalkyl of from 3 to 6 carbon atoms; Het is a 5 or 6 membered ring structure in which 1 or 2 of its members is an oxygen, nitrogen and/or sulfur atom; and $n$ and $n'$ are integers from 1 to 3 the sum of which is equal to 3, 4 or 5 and $m$ is an integer from 1 to 3; and the optical antipodes and pharmaceutically acceptable acid addition salts thereof.

Preferred compounds are those in which Het is thienyl, pyridyl, furyl, thiazolyl, pyrryl, oxazolyl, imidazolyl, or pyrazinyl and $R^1$ is hydrogen or methyl. The most desirable compounds are those in which Het is thienyl.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The compounds within the scope of this invention have both antidepressant and tranquilizing activities. Some have greater pharmaceutical activity than others. Less active compounds are still desirable as intermediates for other compounds, as will become apparent from the following description of several preparations. In these methods, with the exceptions noted, R, R', Het, $n$ and $n'$ are as previously defined and X is halogen, preferably chlorine or bromine.

METHOD A

A 1,3-dihydrospiro[isobenzofuran-cycloazalkane]-3-one of the formula

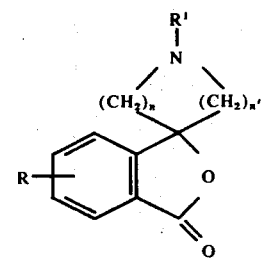

is allowed to react with an organometallic reagent such as a heteroarylmagnesium halide or heteroaryllithium under the normal conditions, e.g., at a temperature of from −60 to 100° C in a solvent such as hexane, toluene, ether or tetrahydrofuran to provide a 1,3-dihydro-3-hydroxyspiro[isobenzofuran-cycloazalkane] of the formula

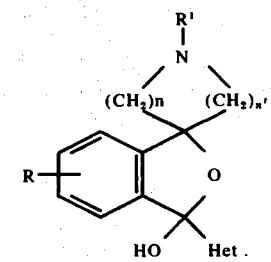

The aforesaid 1,3-dihydrospiro[isobenzofuran-cycloazalkane]-3-one is prepared according to the procedure of method A of U.S. patent application Ser. No. 502,650, now U.S. Pat. No. 3,959,475.

The 1,3-dihydro-3-hydroxyspiro[isobenzofuran-cycloazalkane] is converted by a reducing agent such as lithium aluminum hydride at a temperature of from 0° to 110° C is a solvent such as toluene, ether or tetrahydrofuran to an o-hydroxyalkylphenylcycloazalkanol of the formula

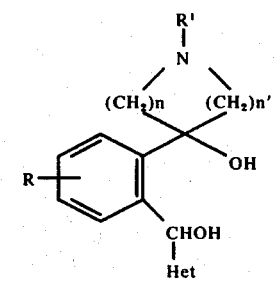

The o-hydroxyalkylphenylcycloazalkanol is treated with an acid, such as hydrochloric, formic, or p-toluenesulfonic acid, preferably in a solvent such as toluene or acetic acid, at a temperature of from 25° to 150° C to provide a compound of the invention, a 1,3-dihydrospiro[isobenzofuran-cycloazalkane], of the formula

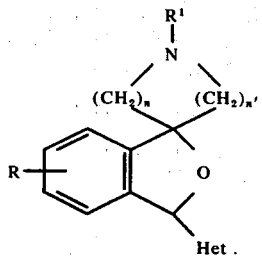

METHOD B

An o-halobenzyl alcohol or its ether of the formula

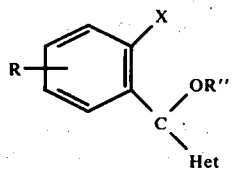

in which R" is hydrogen, alkyl or tetrahydropyranyl is converted, when R" is hydrogen, to the dilithium derivative by treatment with an alkyllithium of preferably from 1 to 6 carbon atoms in a solvent such as ether hexane or tetrahydrofuran or, when R" is alkyl or tetrahydropyranyl, is converted to the lithium derivative or Grignard reagent in the usual manner. The resulting lithium o-lithiobenzalkoxide, o-lithiobenzylether or Grignard reagent is allowed to react with a cycloazalkanone of the formula

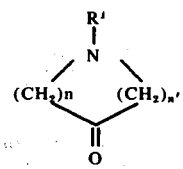

under the reaction conditions which are commonly used for this type of reaction, e.g., at a temperature of from −80 to 20° C., preferably from −80 to 20° C., in a solvent such as ether, tetrahydrofuran, or hexane to provide an o-hydroxyalkylphenylcycloazalkanol or an ether thereof of the formula

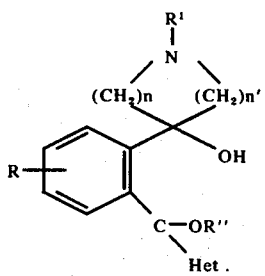

This compound is then cyclized to a 1,3-dihydrospiro-[isobenzofuran-cycloazalkane], a compound of the invention, by acid treatment as in Method A, above.

METHOD C

A 1,3-dihydrospiro[isobenzofuran-cycloazalkane], in which $R^1$ is alkyl or phenalkyl can be treated with a chloroformate, e.g., an alkyl- or phenylchloroformate, at a temperature of from about ambient to 125° C., preferably ambient, in a solvent such as methylene dichloride, toluene or benzene to provide the corresponding N-alkoxycarbonyl or N-phenyloxycarbonyl- 1,3-dihydrospiro[isobenzofuran-cycloazalkane], which is then hydrolyzed with a base such as sodium or potassium hydroxide in a solvent such as water, propanol or a mixture thereof, or with an acid such as hydrogen bromide in acetic acid to provide an N-unsubstituted 1,3-dihydrospiro[isobenzfurancycloazalkane], a compound of the invention.

METHOD D

An N-unsubstituted 1,3-dihydrospiro[isobenzofuran-cycloazalkane] can be reacted in a known manner with an alkanoyl chloride or anhydride, aroyl chloride or anhydride, aralkanoyl chloride, alkyl halide, alkenyl halide, cycloalkanoyl halide, aralkyl halide or aroylalkyl halide, to prove the corresponding N-alkanoyl, N-aroyl, N-aralkanoyl, N-alkyl, N-alkenyl, N-cycloalkanoyl, N-aralkyl or N-aroylalkyl derivative.

METHOD E

The N-alkoxycarbonyl-, N-aryloxycarbonyl-, N-alkanoyl-, N-cycloalkylcarbonyl-, N-aroyl-, N-aralkanoyl- 1,3-dihydrospiro [isobenzofuran-cycloazalkanes] prepared by Methods C and D can be reduced in a known manner with a reagent such as lithium aluminum hydride to the corresponding N-alkyl-, N-cycloalkylalkyl-, or N-aralkanyl-1,3-dihydrospiro[isobenzofuran-cycloazalkanes], compounds of the invention.

The utility of the compounds of the present invention in the treatment of depression in mammals is demonstrated by their ability to inhibit tetrabenazine induced depression in mice [International Journal of Neuropharmacology, 8, 73 (1969)], a standard assay for useful antidepressant properties. Thus, for instance, 1,3-dihydro-3-(2-thienyl)spiro[isobenzofuran-1,4'-piperidine]hydrobromide and 1,3-dihydro-1'-methyl-3-(2-thienyl)-spiro[isobenzofuran-1,4'-piperidine] at intraperitoneal dosages of 2.2 and 3.5 mg/kg of body weight, respectively, demonstrate a 50% inhibition of ptosis of tetrabenzazine-induced depression in mice. These data indicates that the compounds of the present invention would be useful as antidepressants in mammals when administered in amounts ranging from 0.1 to 50 mg/kg of body weight per day.

The additional utility of the compounds of the present invention as tranquilizers due to their depressant action on the central nervous system of mammals is demonstrated in the mouse observation procedure, a standard assay for CNS depressants [Psychopharmacologia, 9, 259 (1966)]. Thus, for instance, the minimum effective dose (MED) at which 1,3-dihydro-1'-methyl-3-(2-thienyl)spiro[isobenzofuran-1,4'-piperidine] and 1,3-dihydro-3-(2-thienyl)spiro[isobenzofuran-1,4'-piperidine] hydrobromide is 10 mg/kg of body weight when administered intraperitoneally.

These data illustrate the compounds of this invention are useful as tranquilizers in mammals when administered in amounts ranging from 0.1 to 50 mg/kg of body weight per day.

Examples of compounds of the invention include:
1,3-dihydro-3-(2-thienyl)-5-ethoxyspiro[isobenzofuran-1,4'-piperidine];
1'-benzyl-5-chloro-1,3-dihydro-3-(3-pyrryl)-spiro[isobenzofuran1,3'-pyrrolidine];
1'-butyl-1,3-dihydro-3-(2-oxazolyl)-6-trifluoromethyl-spiro[isobenzofuran-1,4'-piperidine];
1,3-dihydro-3-(2-imidazolyl)spiro[isobenzofuran-1,4'-piperidine];
1,3-dihydro-5-methoxy-3-(2-thiazolyl)spiro[isobenzofuran-1,4'-piperidine];
1,3-dihydro-6-butoxy-3-(2-pyrazinyl)spiro[isobenzofuran-1,4'-piperidine];
1'-allyl-1,3-dihydro-3-(2-oxazolyl)spiro[isobenzofuran-1,4'-piperidine];
1'-cyclohexylcarbonyl-1,3-dihydro-5-methoxy-3(2-imidazolyl)spiro[isobenzofuran-1,4'-piperidine];
1'-cyclopropylmethyl-1,3-dihydro-3,-(2-pyrazinyl)-spiro[isobenzofuran-1,3'-pyrrolidine];
1'-benzyl-5-ethyl-1,3-dihydro-3-(3-pyrryl)-spiro[isobenzofuran-1,3'-piperidine]; and
1,3-dihydro-3-(2-thienyl)spiro[isobenzofuran-1,3'-piperidine].

Effective quantities of the compounds of the invention may be administered to a patient by any one of various methods, for example, orally as in capsules or tablets, parenterally in the form of sterile solutions or suspensions and in some cases intraveneously in the form of sterile solutions.

The active compounds of the present invention may be orally administered, for example with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–500 milligrams of active compound.

The tablets, pills, capsules, troches, and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as surcrose or saccharin may be added or a flavoring agent such as peppermint, methyl salicyclate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, Shellac, or other enteric coating agents. A syrup may contain, in addition to the active compounds, sucrose as a sweetening agent and certain preservatives, dyes and colorings, and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in ampules, disposable syringes or multiple dose vials made of glass or plastic.

This invention is further illustrated by the following examples.

EXAMPLE I a. A stirring mixture of 154.8 g of 2-bromobenzoic acid, 107.1 g of thionyl chloride and 0.2 ml of dimethylformamide is heated on a steam bath for 45 minutes and then any excess thionyl chloride is distilled off under reduced pressure leaving the crude acid chloride. A mixture of the acid chloride and 60 g of thiophene in 255 g of carbon disulfide is added dropwise to a suspension at 15° C of 100 g of aluminum chloride and 300 g of carbon disulfide. After total addition the mixture is stirred at ambient temperature for 3 hours and then allowed to stand for 16 hours. The stirring mixture is now successively refluxed on a steam bath for 3.5 hours, cooled to ambient temperature and poured over 1 l. of ice followed by dilution with 0.5 l. of water. The biphasic mixture is strained through glass wool to remove any precipitate and then permitted to separate. The aqueous phase is extracted with three 600 ml portions of ether. The ether extracts are combined with the carbon disulfide phase and this mixture is washed with two 500 ml portions of an aqueous 5% sodium carbonate solution followed by washing with two 500 ml portions of water. The organic solution is dried, filtered and then concentrated under reduced pressure leaving a dark oil. The oil is distilled leaving as the main fraction, b.p. 139°–145° C, a green colored oil of 2-(2-bromobenzoyl)thiophene. A solution of 15.0 g of 2-(2-bromobenzoyl)thiophene in 15 ml of absolute ethanol is carefully added with stirring and cooling to a mixture of 2.3 g of sodium borohydride in 40 ml of absolute ethanol. After total addition 15 ml of absolute ethanol is added. The reaction mixture is stirred for 16 hours at ambient temperature and then 50 ml of acetone is added with stirring and the mixture is permitted to stand for 24 hours at ambient temperature. The mixture is poured into 500 ml of water and the resulting mixture acidified with a 5% hydrochloric acid solution causing the mixture to become cloudy. The cloudy mixture is extracted with three 125 ml portions of chloroform which are combined and washed with ten 200 ml portions of water. The chloroform solution is dried and filtered and the chloroform evaporated off leaving α-(2-bromophenyl)-2-thiophenemethanol as an oil.

b. To a stirring mixture of 6.14 g of α-(2-bromophenyl)-2-thiophenemethanol, 17 ml of tetrahydrofuran and 5 ml of hexane under nitrogen cooled at a temperature of −60° C is added over a 25 minute span 23.5 ml of a 2.04 M solution of n-butyllithium in hexane. After total addition the reaction mixture is stirred at −70° C for 15 minutes and then a solution of 2.60 g of 1-methyl-4-piperidone in 10 ml of tetrahydrofuran is added dropwise. The resulting solution is stirred under nitrogen at a temperature from −70° to −40° C for 1.5 hours followed by addition of 15 ml of water containing 1 ml of concentrated HCl. The reaction mixture is poured into a separatory funnel and diluted with water and hexane until an oil separates. The aqueous phase is removed, the organic phase is diluted with additional hexane followed successively by the addition of a little water and trituration until the oil completely solidifies. The water is removed and the resulting suspension suction filtered and the filter cake washed twice with hexane and dried for 16 hours at 40° under reduced pressure. The solid product is recrystallized from toluene to provide colorless crystals, mp 176°–178° C, of 4-hydroxy-4-[α-hydroxy-α-(2-thienyl)-2-tolyl]-1-methylpiperidine.

c. A solution of 0.96 g of 4-hydroxy-4-[α-hydroxy-α-2-thienyl)-2-tolyl]-1-methylpiperidine in 40 ml of aqueous formic acid is refluxed for 2 hours. The resulting green solution is decanted into 200 ml of water and made strongly alkaline by addition of 50% sodium hydroxide solution. The resulting cloudy mixture is extracted thrice with 75 ml of chloroform and the combined extracts are then washed twice with 50 ml of water. The combined extracts are dried overnight under nitrogen, filtered and then the solvent evaporated off leaving an oil. The oil is crystallized from hexane to provide cream colored crystals, mp 65°–68° C, of 1,3-dihydro-1'-methyl-3-(2-thienyl)spiro[isobenzofuran-1,4'-piperidine].

Analysis: Calculated for $C_{17}H_{19}NOS$: 71.53%C; 6.72%H; 4.91%N; 11.23%S. Found: 71.38%C; 6.80%H; 4.92%N; 11.45%S.

EXAMPLE 2

To a solution of 1.26 g of 1,3-dihydro-1'-methyl-3-(2-thienyl)spiro[isobenzofuran-1,4'-piperidine] in 8.0 ml of methylene chloride is added with stirring over a 5 minute span a solution of 0.78 g of phenylchloroformate in 8.0 ml of methylene chloride. After total addition the reaction mixture is stirred under nitrogen for 10 hours. The solvent is removed under reduced pressure leaving an oil which solidifies on trituration with ether. The solid is collected by vacuum filtration, washed with ether and recrystallized from a benzene-hexane mixture to give crystals, mp 142°–147° C, of 1,3-dihydro-1'-phenoxycarbonyl-3-(2-thienyl)-spiro[isobenzofuran-1,4'-piperidine].

Analysis: Calculated for $C_{23}H_{21}NO_3S$: 70.56%C; 5.42%H; 3.58%N; 8.19%S. Found: 70.55%C; 5.55%H; 3.55%N; 3.21%S.

EXAMPLE 3

A mixture of a solution of 2.5 g of potassium hydroxide pellets in a mixed solvent of 0.75 ml of water and 25 ml of n-propyl alcohol and 900 mg of 1,3-dihydro-1'-phenoxycarbonyl-3-(2-thienyl)spiro[isobenzofuran-1,4'-piperidine], under nitrogen is refluxed for 12 hours. The n-propyl alcohol is evaporated off and the residue diluted with 50 ml of water and the aqueous solution is extracted thrice with 50 ml of chloroform. The combined chloroform extracts are dried and filtered and the chloroform removed leaving an oil which is azeotroped with benzene. The oil is triturated with 10 ml of cyclohexane, the cyclohexyl solution filtered and the cyclohexane evaporated off leaving an oil. The oil is dissolved in 25 ml of ether and the hydrobromide salt is precipitated. The salt is collected by vacuum filtration and the filter cake washed twice with ether. The filter cake is recrystallized from a methanol-ether mixture to give a cream colored solid, mp 240°–243° C, dec., of 1,3-dihydro-3-(2-thienyl)spiro[isobenzofuran-1,4'-piperidine]hydrobromide.

Analysis: Calculated for $C_{16}H_{17}NOS\cdot HBr$: 54.54%C; 5.16%H; 3.98%N; 22.68%Br. Found: 54.47%C; 5.11%H; 3.93%N; 22.86%Br.

EXAMPLE 4 a. A mixture of 31.6 g of 3-bromopyridine and 21.8 g of ethyl bromide in 250 ml of tetrahydrofuran is added dropwise to 9.8 g of magnesium in 150 ml of tetrahydrofuran. After total addition, the reaction mixture is heated at 50° C for 6 hours and then cooled to 20° C. To the Grignard solution is added dropwise a solution of 74.0 g of o-bromobenzaldehyde in 150 ml of tetrahydrofuran. After total addition, the mixture is heated momentarily at 60° C, allowed to cool to ambient temperature and then poured into 2 liters of dilute ammonium chloride solution. This mixture is extracted with benzene and the benzene extracts in turn extracted with 20% hydrochloric acid. The acidic layer is basified with 30% sodium hydroxide solution and then extracted with benzene, and the benzene removed leaving a highly crystalline product. The product is recrystallized from methanol leaving colorless crystals, mp 121°–124° C, of α-(2-bromophenyl)-3-pyridinemethanol.

b. A sample of 2.10 g of α-(2-bromophenyl)-3-pyridinemethanol is dissolved in methanol and added to a solution of 0.23 g of sodium in methanol. After stirring briefly, the methanol is removed at reduced pressure and the residue dissolved in dimethylsulfoxide. This solution is permitted to stir, to it is added dropwise 0.95 ml of dimethyl sulfate, after total addition it is heated briefly at 85° C, and permitted to cool. The reaction mixture is poured into water and the aqueous solution is acidified with 3N hydrochloric acid. The solution is extracted with an ether-benzene mixture and basified with 30% sodium hydroxide. The basified solution is then extracted with benzene. The combined extracts are dried and the solvent removed leaving a brownish oil. The oil is purified by column chromatography on alumina (1% methanol in benzene as eluant) to provide α-(2-bromophenyl)-α-methoxy-3-methylpyridine.

c. A sample of 4.5 g of α-(2-bromophenyl)-α-methoxy-3-methylpyridine is dissolved in a mixture of 35 ml of tetrahydrofuran and 15 ml of n-hexane. The mixture is cooled to −65° C under nitrogen and 10 ml of a 2.2 M solution of n-butyllithium are added dropwise. After total addition, a solution of 2.5 g of 1-methyl-4-piperidone in 25 ml of tetrahydrofuran is added dropwise. Again after total addition the reaction mixture is maintained at from −70° to −55° C for 2–3 hours and is then allowed to gradually reach ambient temperature. The mixture is allowed to stir for 16 hours, cooled to 0° C, and then 1.5 ml of concentrated hydrochloric acid and 10 ml of water are added quickly. A biphasic mixture results which is poured into 100 ml of ether and acidified by shaking with a 5% hydrochloric acid solution. The ether layer is removed and the aqueous layer is basified by addition of 10.0% sodiumhydroxide solution and followed by extraction with benzene. The combined benzene extracts are washed with water and dried and the solvent removed leaving a viscous orange oil. The oil is dissolved in ethanol and a 5.0% solution of oxalic acid in isopropyl alcohol is added. The oxalate precipitates and is collected by filtration and dried. The filter cake is dried and the salt is broken by crystallization from ethanol leaving the free base as a viscous oil. The oil is crystallized from n-heptane to give the colorless solid, mp 141.0°–142.0° C, of α-[2-(4-hydroxy-1-methylpiperidin-4-yl)phenyl]-α-methoxy-3-methylpyridine.

d. To a stirred solution of 0.90 g of α-[2-(4-hydroxy-1-methylpiperidin-4-yl)phenyl]-α-methoxy-3-methylpyridine in 60 ml of glacial acetic acid is added 1 ml of concentrated sulfuric acid. The solution is refluxed for five hours and permitted to cool and then diluted with water and neutralized with a 30% sodium hydroxide solution. The reaction mixture is extracted with a benzene-ethyl acetate mixture and the combined extracts are washed with water, dried and filtered. The filtrate is concentrated leaving an oil which is dissolved in ethanol and filtered. The ethanol is removed leaving a dark viscous oil which is dried at 80° C in high vacuum for 6 hours to provide the amorphous product of 1,3-dihydro-1′-methyl-3-(3-pyridyl)spiro[isobenzofuran-1,4′-piperidine].

Analysis: Calculated for $C_{18}H_{20}N_2O$: 77.11%C; 7.19%H; 9.99%N. Found: 75.97%C; 6.60%H; 9.76%N.

EXAMPLE 5 a. 2.5 ml of a 2.4 M solution of n-butyl-lithium in hexane is added to a stirred solution of 0.41g of furan and 5 ml of ether under nitrogen at −50° C. The resultant solution is heated under reflux with exclusion of moisture for 40 minutes during which time a precipitate separates. The reaction mixture is cooled to −20° C.; treated with a solution of 1.46 g of 1′-benzyl-1,3-dihydrospiro[isobenzofuran-1,4′-piperidine]-3-one in 5 ml each of tetrahydofuran and ether, and stirred while permitting the temperature to reach 20° C.; at which time 8 ml of water at 5° C are added. The mixture is further diluted with water and extracted three times with 30 ml of chloroform. The combined extracts are washed with water and dried and the chloroform evaporated off leaving a solid residue. The residue is recrystallized from acetonitrile to provide cream colored crystals, mp 146°–148° C, of 1′-benzyl-1,3-dihydro-3-(2-furyl)-3-hydroxyspiro-[isobenzofuran-1,4′-piperidine].

Analysis: Calculated for $C_{23}H_{23}NO_3$: 76.42%C; 6.43%H; 3.88%N. Found: 76.34%C; 6.38%H; 3.80%N.

b. A solution of 3.0g of 1′-benzyl-1,3-dihydro-3-(2-furyl)-3-hydroxyspiro[isobenzofuran-1,4′-piperidine] in 30 ml of tetrahydrofuran is added, over a 30 minute span with water bath cooling, to a stirred mixture of 0.9 g of lithium aluminum hydride and 60 ml of tetrahydrofuran. After addition is complete, the mixture is stirred for 40 minutes at ambient temperature and at 50° C for an additional 30 minutes. The mixture is decanted portionwise onto 200 ml of ice, diluted with water and the ice-water mixture is extracted thrice with 100 ml of chloroform. The combined extracts are washed with 100 ml of water and dried and the chloroform is evaporated off, leaving an oil which forms a tacky foam upon standing. The foam is dissolved in 40 ml of aqueous formic acid (prepared diluting 35 ml of 97% formic acid with water) and the solution is maintained at a temperature of 48° C with occasional agitation for 2 hours and then poured into 300 ml of water. The aqueous mixture is basified with a 50% sodium hydroxide solution and then extracted thrice with 100 ml of chloroform. The combined extracts are dried and the chloroform is evaporated off, leaving a viscous oil. The oil is dissolved in 30 ml of ether and precipitated as its hydrochloride salt. The salt is collected by suction filtration and the filter cake is washed with ether and dried in vacuo at 40° C for 4 hours. The dried salt is recrystallized twice from isopropyl alcohol to provide cream colored crystals, mp of 234°–236° C, of 1′-benzyl-1,3-dihydro-3-(2-furyl)spiro[isobenzofuran-1,4′-piperidine]hydrochloride.

Analysis: Calculated for $C_{23}H_{23}NO_2HCl$: 72.32%C; 6.35%H; 3.67%N; 9.28%Cl. Found: 71.79%C; 6.14%H; 3.46%N; 9.87%Cl.

EXAMPLE 6

By successively following the procedures of Examples 2 and 3, a sample of 1,3-dihydro-1′-methyl-3-(3-pyridyl)spiro[isobenzofuran-1,4′-piperidine], Example 4, is treated to ultimately provide 1,3-dihydro-3-(3-pyridyl)spiro[isobenzofuran-1,4′piperidine]hydrobromide,

EXAMPLE 7

A mixture of 0.1 mole each of 1,3-dihydro-3-(2-thienyl)spiro[isobenzofuran-1,4′-piperidine], free base of Example 8, and ω-chloro-p-fluorobutyrophenone ethylene ketal, 10g of potassium carbonate and 50 ml of butanol is heated under reflux for 46 hours and filtered. The filtrate is concentrated and the residue is stirred with 50 ml of 3N hydrochloric acid and 50 ml of ethanol. The mixture is basified with sodium hydroxide and extracted with benzene. The combined benzene extracts are dried and the benzene is evaporated off, leaving 1,3-dihydro-1′-[3-(p-fluorobenzoyl)propyl]-3-(2-thienyl)spiro[isobenzofuran-1,4′-piperidine].

We claim:

1. A compound of the formula

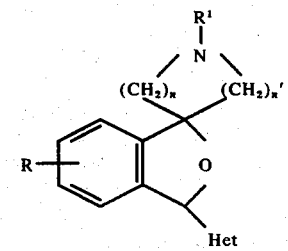

wherein R is hydrogen, alkyl of from 1 to 6 carbon atoms, alkoxy of from 1 to 6 carbon atoms, trifluoromethyl or halogen; $R^1$ is hydrogen, alkyl of from 1 to 6 carbon atoms, phenalkyl of from 7 to 9 carbon atoms, benzoylalkyl of the formula $-(CH_2)_m-COPhR$, phenoxy carbonyl, alkoxycarbonyl of from 2 to 7 carbon atoms, alkenyl of from 2 to 6 carbon atoms, cycloalkylcarbonyl of from 4 to 7 carbon atoms or cycloalkylalkyl of from 3 to 6 carbon atoms; Het is thienyl, pyridyl, furyl, thiazolyl, pyrryl, oxazolyl, imidazolyl or pyrazinyl; $n$ and $n'$ are integers from 1 to 3, the sum of which is equal to 3, 4 or 5; and $m$ is an integer from 1 to 3; or an optical antipode or a pharmaceutically acceptable acid addition salt thereof.

2. A compound as defined in claim 1 wherein the sum of $n$ and $n'$ is equal to 3 or 4.

3. A compound as defined in claim 1 wherein the sum of $n$ and $n'$ is equal to 4.

4. A compound as defined in claim 1 wherein Het is thienyl.

5. A compound as defined in claim 4 wherein the sum of $n$ and $n'$ is equal to 4.

6. A compound as defined in claim 5 wherein R is hydrogen; and $R^1$ is hydrogen, methyl, benzyl, phenoxycarbonyl or p-fluorobenzoylpropyl.

7. A compound as defined in claim 6 wherein $R^1$ is benzyl, phenoxycarbonyl or p-fluorobenzoylpropyl.

8. A compound as defined in claim 1 wherein R is hydrogen.

9. A compound as defined in claim 8 wherein Het is thienyl, pyridyl, furyl or thiazolyl.

10. A compound as defined in claim 9 wherein $R^1$ is hydrogen, methyl, benzyl, phenoxycarbonyl or p-fluorobenzoylpropyl.

11. A compound as defined in claim 10 wherein $R^1$ is benzyl, phenoxycarbonyl or p-fluorobenzoylpropyl.

12. A compound as defined in claim 8 wherein Het is pyridyl, furyl or thiazolyl.

13. A compound as defined in claim 12 wherein the sum of $n$ and $n'$ is equal to 4.

14. A compound as defined in claim 13 wherein $R^1$ is hydrogen, methyl, benzyl, phenoxycarbonyl or p-fluorobenzoylpropyl.

15. A compound as defined in claim 14 wherein $R^1$ is benzyl, phenoxycarbonyl or p-fluorobenzoylpropyl.

16. The compound defined in claim 1 which is 1,3-dihydro-3-(2-thienyl)spiro[isobenzofuran-1,4'-piperidine].

17. The compound defined in claim 1 which is 1,3-dihydro-1'methyl-3-(2-thienyl)spiro[isobenzofuran-1,4'-piperidine].

18. The compound defined in claim 1 which is 1,3-dihydro-1'methyl-3-(3-pyridyl)spiro[isobenzofuran-1,4'-piperidine].

19. The compound defined in claim 1 which is 1'-benzyl-1,3-dihydro-3-(2-furyl)spiro[isobenzofuran-1,4'-piperidine].

20. The compound defined in claim 1 which is 1,3-dihydro-1'-[3-(p-fluorobenzoyl)propyl]-3-(2-thienyl)-spiro[isobenzofuran-1,4'-piperidine].

21. The compound defined in claim 1 which is 1,3-dihydro-1'-phenoxycarbonyl-3-(2-thienyl)-spiro[isobenzofuran-1,4'-piperidine].

22. A method of treating depression which comprises administering to a patient in need of such treatment a pharmaceutically effective amount of a compound as defined in claim 1.

23. A method of treating depression which comprises administering to a patient in need of such treatment a pharmaceutically effective amount of a compound as defined in claim 4.

24. A method of treating depression which comprises administering to a patient in need of such treatment a pharmaceutically effective amount of a compound as defined in claim 6.

25. A method of treating depression which comprises administering to a patient in need of such treatment a pharmaceutically effective amount of 1,3-dihydro-3-(2-thienyl)spiro[isobenzofuran-1,4'-piperidine].

26. A method of treating depression which comprises administering to a patient in need of such treatment a pharmaceutically effective amount of 1,3-dihydro-1'-methyl-3-(2-thienyl)spiro[isobenzofuran-1,4'-piperidine].

27. A method of tranquilizing the central nervous system which comprises administering to a patient in need of such treatment a pharmaceutically effective amount of a compound as defined in claim 1.

28. A method of tranquilizing the central nervous system which comprises administering to a patient in need of such treatment a pharmaceutically effective amount of a compound as defined in claim 6.

29. A method of tranquilizing the central nervous system which comprises administering to a patient in need of such treatment a pharmaceutically effective amount of 1,3-dihydro-3-(2-thienyl)spiro[isobenzofuran-1,4'-piperidine].

30. A method of tranquilizing the central nervous system which comprises administering to a patient in need of such treatment a pharmaceutically effective amount of 1,3-dihydro-1'-methyl-3-(2-thienyl)-spiro[isobenzofuran-1,4'-piperidine].

31. A pharmaceutical composition which comprises between about 0.5 and about 70 percent by weight of a compound defined in claim 1 as an essential active ingredient, the balance being a pharmaceutically acceptable carrier therefor.

32. A pharmaceutical composition which comprises between about 0.5 and about 70 percent by weight of a compound defined in claim 4 as an essential active ingredient, the balance being a pharmaceutically acceptable carrier therefor.

33. A pharmaceutical composition which comprises between about 0.5 and about 70 percent by weight of a compound defined in claim 6 as an essential active ingredient, the balance being a pharmaceutically acceptable carrier therefor.

34. A pharmaceutical composition which comprises between about 0.5 and about 70 percent by weight of 1,3-dihydro-3-(2-thienyl)spiro[isobenzofuran-1,4'-piperidine] as an essential active ingredient, the balance being a pharmaceutically acceptable carrier therefor.

35. A pharmaceutical composition which comprises between about 0.5 and about 70 percent by weight of 1,3-dihydro-1'-methyl-3-(2-thienyl)spiro[isobenzofuran-1,4'-piperidine].

* * * * *

UNITED STATES PATENT AND TRADEMARK OFFICE
CERTIFICATE OF CORRECTION

PATENT NO. : 4,031,224
DATED : June 21, 1977
INVENTOR(S) : Lawrence Leo Martin et al.

It is certified that error appears in the above-identified patent and that said Letters Patent are hereby corrected as shown below:

In the Heading (Item [54]) and in Column 1, line 1, in the title, "(ISOBENZOFURAN)S" should be --[ISOBENZOFURAN]S--;

Column 1, line 27, "U. S. Pat. No. 3,595,475" should be --U. S. Pat. No. 3,959,475--;

Column 1, line 30, after "August 29, 1974" insert --now U. S. Patent No. 3,957,828--;

Column 1, line 40, in the structural formula, "R" should be inserted to appear as follows:

Column 3, line 34, after "ether" add a comma (,);

Column 3, line 51, "20°C." (second occurrence only) should be -- -20°C--;

Column 4, line 18, "[isobenzfuran" should be --[isobenzofuran--;

Column 4, line 27, "prove" should be --provide--;
Column 4, line 49, "(2-thienyl)-spiro" should be --(2-thienyl)spiro--;

Column 5, line 20, "methoxy-3(2-" should be --methoxy-3-(2- --;

Column 5, line 23 "dihydro-3,-(2-" should be --dihydro-3-(2- --;

UNITED STATES PATENT AND TRADEMARK OFFICE
CERTIFICATE OF CORRECTION

PATENT NO. : 4,031,224
DATED : June 21, 1977
INVENTOR(S) : Lawrence Leo Martin et al.

It is certified that error appears in the above-identified patent and that said Letters Patent are hereby corrected as shown below:

Column 5, line 66, "Shellac" should be --shellac--;

Column 7, line 33, "2-thienyl)-2-" should be --(2-thienyl)-2- --;

Column 9, line 13, "sodiumhydroxide" should be --sodium hydroxide--;

Column 9, lines 24 and 29, in each instance, "piperidin-4-yl)" should be --piperidine-4-yl)--;

Column 9, line 62, "hydroxyspiro-[isobenzo" should be --hydroxyspiro[isobenzo--;

Column 10, line 39, the comma (,) after "hydrobromide" should be a period (.).

Signed and Sealed this

Sixth Day of December 1977

[SEAL]

Attest:

RUTH C. MASON
Attesting Officer

LUTRELLE F. PARKER
Acting Commissioner of Patents and Trademarks